(12) United States Patent
Lee

(10) Patent No.: US 7,608,287 B2
(45) Date of Patent: Oct. 27, 2009

(54) GINSENG WINE

(75) Inventor: In Sung Lee, 5 Kenneth Ave. Unit #1206, Toronto, Ontario (CA) M2N 6M7

(73) Assignee: In Sung Lee, Toronto, Ontario (CA)

( * ) Notice: Subject to any disclaimer, the term of this patent is extended or adjusted under 35 U.S.C. 154(b) by 0 days.

(21) Appl. No.: 11/163,296

(22) Filed: Oct. 13, 2005

(65) Prior Publication Data

US 2007/0087062 A1   Apr. 19, 2007

(51) Int. Cl.
*A61K 36/254* (2006.01)
*A61K 36/258* (2006.01)

(52) U.S. Cl. .................................. 424/728

(58) Field of Classification Search ............ None
See application file for complete search history.

(56) References Cited

FOREIGN PATENT DOCUMENTS

| JP | 03210172 | A  | * | 9/1991 |
| JP | 03277246 | A2 |   | 12/1991 |
| JP | 05023149 | A2 |   | 2/1993 |
| JP | 10295357 | A2 |   | 11/1998 |

OTHER PUBLICATIONS

Retrieved from http://web.archive.org/web/*/http://www.quickchange.com/ginsengstore/faqs.html. Internet Archive Date: Mar. 8, 2000, [Retrieved from the Internet: Jan. 28, 2008].*
'The Winemaking Home Page. Winemaking: the Basic Steps.'. Last updated: Nov. 2, 2000, Internet Archive Wayback Machine Date: Feb. 3, 2001 [retrieved on Jul. 24, 2007]. Retrieved from the Internet: <URL: http://web.archive.org/web/20010203235600/http://winemaking.jackkeller.net/basics.asp> pp. 1 and 2.*
'The Winemaking Home Page. Winemaking: the Basic Steps. Extracting Flavor.' Last Updated: Aug. 29, 2004. Internet Archive Wayback Machine Date: Sep. 6, 2004 [retrived on Jul. 24, 2007]. Retrieved from the Internet: <URL: http://web.archive.org/web/*/http://winemaking.jackkeller.net/extracting.asp> pp. 2 and 3.*
'The Winemaking Home Page. Winemaking: the Basic Steps. Additives and Other Ingredients.' Last Updated: Aug. 29, 2004 [retrived on Jul. 24, 2007]. Retrieved from the Internet: <URL: http://winemaking.jackkeller.net/adding.asp> pp. 1-3.*
'The Winemaking Home Page. Winemaking: the Basic Steps continued. Using your hydrometer.' Last Updated: Nov. 6, 2000. Internet Archive Wayback Machine Date: Apr. 9, 2001 [retrived on Jul. 24, 2007]. Retrieved from the Internet: <URL: http://web.archive.org/web/20010409193646/http://winemaking.jackkeller.net/hydrom.asp> pp. 1-7.*
Retrieved from :http://web.archive.org/web/*/http://www.wynboer.co.za/recentarticles/0411enzymes.php3. Internet Archive Date: Dec. 9, 2004 [Retrieved from the Internet: Jan. 28, 2008].*
A. R. Harding. Ginseng and Other Medicinal Plants. A.R. Harding: Ohio, 1908. p. 156.*
Herbal Supplements. Internet Archive Date: Jun. 6, 2002 [Retrieved on: Sep. 15, 2008]. Retrieved from: <http://web.archive.org/web/20020606221610/http://spineuniverse.com/displayarticle.php/article1064.html>. p. 1.*
Pesgens, M. The Home Winemaking Book, 2000. Retrieved from the Internet: <http://www.geocities.com/mipeman/download/thwb.pdf>.

* cited by examiner

*Primary Examiner*—Christopher R Tate
*Assistant Examiner*—Amy L Clark
(74) *Attorney, Agent, or Firm*—Joseph H. Kim; JHK Law

(57) ABSTRACT

The present application discloses a process for making ginseng wine.

17 Claims, No Drawings

GINSENG WINE

BACKGROUND OF THE INVENTION

1. Field of the Invention

The present invention relates to a process for the production of ginseng wine.

2. General Background and State of the Art

Ginseng is a human-shaped root that is one of the most popular healing herbs of the East and West used to combat weakness and give extra energy. Ginseng, prized for millennia, has an ancient history and now it is an extremely popular herb with a wide range of therapeutic uses.

The genus name Panax is derived from the Latin word "panacea" meaning "cure-all" (Named by German scientist C.A. Meyer in 1842).

Since the 1940s, ginseng has been one of the most highly researched herbs in the world. There are more than three thousand scientific studies performed on ginseng. Results of many high level health studies throughout the world demonstrate that ginseng possesses a large variety of therapeutic effects on the body including benefits to the central nervous system, cardiovascular system, stress (mental and emotional), fatigue, aging, and so on.

In recent years, ginseng has been promoted in the West as a tonic and a rejuvenator. Thus, there is strong evidence that ginseng has many positive effects on the body and the mind.

Ginseng species includes Panax ginseng (Korean ginseng), Panax quinquefolius (North American ginseng), Panax japonicum (Japanese ginseng), Panax notoginseng (san-qi ginseng), and Panax pseudoginseng (Himalayan ginseng).

Siberian ginseng (*Eleutherococcus senticosus*) is actually not a true ginseng species, but the properties and uses of all of these are similar and are generally referred to as ginseng.

Results of one study showed that the administration of Panax ginseng extract at doses of 3 g/65 Kg body weight 40 minutes after the last drink enhanced the rate of blood alcohol clearance in healthy male volunteers.

Some of the main chemical components of ginseng include at least 1 3 different saponins, collectively known as ginsenosides; starch; glycosides; sterols; volatile oil; polysaccharides; minerals; various flavonoids; vitamin—Bs (thiamin, riboflavin, niacin, pantothenic acid, and cobalamin); biotin; choline; pectin; phytoestrogens; and simple sugars (glucose, fructose, sucrose, maltose, and trisaccharides). It should be noted that the components may vary depending on the species and the age of the plant.

Possible therapeutic benefits of Ginseng include:

1) Stimulant: Ginseng improves mental performance, especially in older people. Ginseng contains choline, a chemical in the brain that is essential for learning and memory retention.

2) Antioxidant: Ginseng contains antioxidants, substances that prevent cellular damage due to oxidation, exposure to unstable molecules called free radicals.

3) Antiaging: Ginseng exhibited antisenility effects and led to the relief of age-related symptoms in a group of middle aged and elderly subjects.

4) Anticancer: Results of many studies found that unpurified saponins, compounds found in ginseng, inhibited the growth of cancer cells and actually converted diseased cells into normal cells. Ginseng also helps the body to cope with the side effects of chemotherapy.

5) Adaptogenic: Ginseng's remarkable 'adaptogenic' quality (helping the body to adapt to stress, fatigue, and cold) has been confirmed.

6) Menopause: Ginseng contains compounds that are similar in action to estrogen, the female sex hormone.

7) Antidiabetic: Ginseng helps the body maintain normal blood sugar and cholesterol level, and stimulates a range of immune system and endocrine responses.

Therefore, there is a need in the art to make beverages such as wine that imparts nutritional and health benefits of ginseng.

SUMMARY OF THE INVENTION

In one aspect of the invention, ginseng wine may be produced by the following steps:

(i) combining ground ginseng, boiling water and sugar in a sterilized primary fermentor to form a mixture;

(ii) measuring specific gravity of the mixture when the temperature of the mixture reaches room temperature, and adding purified cool water and/or sugar until the specific gravity reaches a level between 1.120 and 1.080;

(iii) adding yeast or yeast culture to the mixture and stirring the mixture to add oxygen and to release accumulated heat created during primary fermentation;

(iv) racking off lees of the wine into a sterilized secondary fermentor for anaerobic fermentation when the specific gravity reading after the primary fermentation reaches between 1.020 or less, and anaerobically fermenting the wine;

(v) racking the wine at a specific gravity reading of about 0.998 to about 0.995 after the anaerobic fermentation into a sterilized container, and further anaerobically fermenting the wine; and (vi) racking the wine again into a sterilized container to achieve the clearer and clean-tasting wine.

In this process, the ground ginseng may be fresh ginseng or boiled ginseng. Preferably, the ground ginseng is fresh ginseng. Further, the ground ginseng may be boiled and simmered for about 15-30 minutes before the fermentation. In one embodiment of the invention, in step (i) above, the ginseng may be present in the mixture at about 0.05 Kg to about 0.2 Kg per liter of water, preferably at about 0.08 Kg to about 0.15 Kg per liter of water.

In another embodiment of the invention, in steps (i)-(ii), the sugar may be included in the mixture at about 0.15 Kg to about 0.45 Kg per liter of water, preferably from about 0.2 Kg to about 0.4 Kg per liter of water.

In another aspect of the invention, an acidic substance may be added to the mixture in step (ii), and the acidic substance may be citric juice such as lemon juice.

Still further, tannin or sulfur dioxide may be added to the mixture in step (ii), wherein if sulfur dioxide is added, the mixture may be allowed to settle for about 24 hours.

In further other aspect of the invention, in step (ii), the maximum amount of sugar added may be about 0.4 Kg per liter of water.

Further in the process described above, in step (iii), the primary fermentation may be carried out at about 18 to about 26 degrees C., preferably for about seven to twelve days.

In yet another embodiment, in step (iv) of the process described above, the secondary fermentation may be carried out at about 15 to 23 degrees C., preferably for about two to three weeks. A fining agent may be added to the wine.

In further another embodiment, the invention is directed to the wine produced by the above described process.

DETAILED DESCRIPTION OF THE INVENTION

In the present application, "a" and "an" are used to refer to both single and a plurality of objects.

As used herein, "fining agent" refers to adsorptive or reactive substance to reduce or remove the concentration of one or more undesirable components in the wine. Fining agents are used to achieve clarity and to improve color, flavor and physical stability. Fining agents can be grouped according to their chemical nature and mode of action, such as 1. Earths: bentonite; 2. Proteins: gelatin, isinglass, casein, albumen; 3. Polysaccharides: agars; 4. Carbons; 5. Synthetic polymers: PVPP; 6. Silicon dioxide (kieselsol); and 7. Others, including chelators and enzymes.

As used herein, "free-run wine" refers to the ginseng wine before undergoing pressing.

As used herein, "lees" refers to solids that result from fermentation, that are found on the bottom of the container.

As used herein, "stabilizing agent" refers to an agent that is added to the wine to eliminate the risk of microbial spoilage, to reduce the effects of oxidation, to ensure fermentation does not re-occur in sweet wine, and to maintain color stability and clarity throughout the aging process.

Ingredients of ginseng wine (For about 6 U.S. gallons/23 liters of wine)

Fresh ginseng roots: 2-3 Kg
Water (purified): 20-24 liters
Sugar: 5.0-8.0 Kg
Wine yeasts: 5-10 g
Acids (tartaric, citric, or acid blends (with tartaric/malic/citric acids): 3.0-3.9 pH
Sulfur dioxide (optional): 30-50 ppm
Tannin (optional): 8-12 g
Fining agents (optional): Pectic enzyme, bentonite, amylase or diastase, isinglass, and/or tannins (use according to the directions provided by the maker).
Stabilizers: Potassium sorbate (125-200 ppm) or wine conditioner (up to 250 ml)

Winemaking Process

The process of making ginseng wine is described below, however, it is understood that a variation in the order of the steps is contemplated within the scope of the invention so long as ginseng wine is made. Further, the process exemplified here is directed to making about 23 liters or 6 gallons of wine, which can be scaled up or down as desired.

The fresh ginseng roots are rinsed thoroughly to remove soil, harmful bacteria, insects, and any chemical residues. Any moldy and brown spots should be cut out. The washed ginseng roots are ground after adding 3-4.5 liters of cold water. The ground ginseng roots can be optionally boiled before the fermentation. If boiled, the ground ginseng is brought to a boil in 6-9 liters of water and then simmered for about 15-30 minutes over medium heat.

The ground ginseng roots are then placed in a sterilized primary fermentor (vessel for aerobic fermentation which is the initial and rapid fermentation) and combined with boiling water (3-5 liters) in which sugar is dissolved. In particular, the sugar to be used may be a fermentable sugar such as dextrose (corn sugar) or sucrose (beet or cane sugar).

When the mixture has cooled down to room temperature, the specific gravity reading should be taken. Purified cool water and/or sugar is added until the specific gravity reading of the mixture reaches a level between 1.080 and 1.120 to get about 11 to 17 percent alcohol rate.

Acids are added to the mixture, and tannins and sulfur dioxide can also be added if desired. If sulfur dioxide is added, the sulfited mixture is allowed to settle for about twenty-four (24) hours.

Wine yeasts (or yeast culture) are added to the mixture and the fermentor should be covered to protect the mixture from any insect and dust. The mixture is allowed to stand at around 18-26 degrees C. (65-80 degrees F.).

During the primary fermentation, the cap (the layer of solid ginseng contents that forms on top of the mixture) should be punched down and the mixture stirred several times a day to 1) mix the ginseng contents with the mixture to impart ingredients and flavor; 2) introduce a limited amount of oxygen required by the growing population of yeasts during the vigorous initial fermentation; and 3) release the accumulated heat created by the fermentation.

When the fermentation has subsided after seven to twelve days of vigorous primary fermentation (at specific gravity reading of 1.020 or less), the wine is racked off the lees into the sterilized secondary fermentor (vessel for anaerobic fermentation which is slower fermentation). The remaining lees are pressed to release additional wine which is richer in desirable extracts and ginseng flavors than the free-run. This pressed wine is added to the free-run wine.

The secondary fermentor should be filled leaving enough room between the surface of the wine and the bottom of the fermentation lock to prevent the wine from overflowing. Ginseng forms many bubbles because of its components, including saponins known as ginsenosides.

The airlock (fermentation lock) should be installed on the fermentor to protect the wine from contact with air while still allowing the carbon dioxide gas to escape. The airlock may be filled with water or sulfite solution to approximately half full in each chamber.

The wine is allowed to stand at around 15-23 degrees C. (60-75 degrees F.) for two to three weeks for the secondary fermentation until the specific gravity has fallen to 0.998-0.995, at which time the wine is racked again into another sterilized container, leaving behind as much lees as possible. The new container should be filled as fully as possible. If the container is not filled, it may be preferably filled with purified cool water, or sugar water, or same kind of wine. And the container should be closed with an airlock. During this stage, sluggish fermentation may occur.

When the fermentation process is completely over, there is no more activity inside the air-lock. The specific gravity reading should be taken to check the alcohol levels. The wine can be racked again into another sterilized container to achieve the clearer and clean-tasting wine.

Correctly made ginseng wine should not normally require a clarification process. But, if the wine remains cloudy after two to three months after fermentation has ceased, there is a possibility that it will not clear naturally. In this case, a clarification process should be performed with proper fining agents. Filtration is another option for clarification and stabilization as well.

The wine should be stabilized even after successful fermentation to prevent the possibility of refermentation after bottling. There are several stabilization methods, such as adding stabilizing agent, filtration, pasteurization, cold stabilization, and centrifuging (for the large volume of wine).

The wine is allowed to stand for several months in a cool and dark place for bulk aging. After several months of bulk aging, 30 ppm of sulfur dioxide is added if desired, and the wine is then bottled and aged in a cool and dark place. If the wine has not already gone through the filtration process, the wine can be filtered before the bottling. At this point, the wine could have about 11-17% alcohol by volume. The wine will be quite drinkable soon after bottling but will improve with bottle aging in a cool place for a while.

Ginseng wine may be served at room temperature, chilled, or warm (but never boiled) as a versatile drink before, during and after meals. The amount of ethanol alcohol actually formed depends on the several factors including the amount of sugar, nutrient level of the materials (ginseng in this case), yeast species, and the general condition of fermentation. If the mixture is too rich with sugar, it may actually retard fermentation and clarification.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A process for the preparation of ginseng wine, said process comprising
   (i) grinding fresh ginseng root to produce ground ginseng root, optionally boiling said ground ginseng root, and combining said ground ginseng root or boiled ground ginseng root with boiling water and sugar in a sterilized primary fermentor to form a mixture;
   (ii) measuring specific gravity of the mixture when the temperature of the mixture reaches room temperature, and adding purified cool water and/or sugar until the specific gravity reaches a level between 1.120 and 1.080;
   (iii) adding yeast or yeast culture to the mixture and stirring the mixture to add oxygen and to release accumulated heat created during primary fermentation;
   (iv) punching down a layer of solid ginseng content that forms on top of the mixture during the primary fermentation and stirring the mixture to impart ingredients and flavor from the solid ginseng to the mixture;
   (v) after primary fermentation until the specific gravity reading reaches 1.020 or less, racking free-run wine off lees of the primary fermentation mixture into a sterilized secondary fermentor;
   (vi) pressing said lees to release additional wine which is combined with the free-run wine and anaerobically fermenting the wine in the secondary fermentor;
   (vii) racking the wine at a specific gravity reading of about 0.998 to about 0.995 after the anaerobic fermentation into a sterilized container, and further anaerobically fermenting the wine; and
   (viii) racking the wine again into a sterilized container to produce ginseng wine.

2. The process according to claim 1, wherein the ground ginseng root is boiled.

3. The process according to claim 1, wherein the fresh ginseng root is rinsed before said grinding.

4. The process according to claim 1, wherein in (i), the ground ginseng root is boiled and simmered for about 15-30 minutes before the fermentation.

5. The process according to claim 1, wherein in (i), the ground ginseng root is present in the mixture in an amount of about 0.05 to about 0.2 kilogram of ginseng root per liter of water.

6. The process according to claim 5, wherein the ground ginseng root is present in the mixture in an amount of about 0.08 to about 0.15 kilogram of ginseng root per liter of water.

7. The process according to claim 1, wherein in (i) and (ii), the sugar is included in the mixture in an amount of about 0.15 to about 0.45 kilogram of sugar per liter of water.

8. The process according to claim 1, wherein in (i) and (ii), the sugar is included in the mixture in an amount of about 0.2 to about 0.4 kilogram of sugar per liter of water.

9. The process according to claim 1, wherein in (ii), the maximum amount of sugar added is in an amount of about 0.4 kilogram of sugar per liter of water.

10. The process according to claim 1, wherein in (iii), the primary fermentation is carried out at about 18 to about 26 degrees C.

11. The process according to claim 10, wherein in (iii), the primary fermentation is carried out for about seven to twelve days.

12. The process according to claim 1, wherein in (iv), the secondary fermentation is carried out at about 15 to 23 degrees C.

13. The process according to claim 12, wherein in (iv), the secondary fermentation is carried out for about two to three weeks.

14. The process according to claim 1, comprising adding a fining agent to the wine, if the wine is cloudy.

15. The process according to claim 1, wherein pH of the wine is in the range of 3.0 to 3.9.

16. A process for the preparation of ginseng wine with an alcohol content of 11 to 17%, said process comprising
   (i) grinding fresh ginseng root to produce ground ginseng root, optionally boiling said ground ginseng root, and combining said ground ginseng root or boiled ground ginseng root with boiling water and sugar in a sterilized primary fermentor to form a mixture;
   (ii) measuring specific gravity of the mixture when the temperature of the mixture reaches room temperature, and adding purified cool water and/or sugar until the specific gravity reaches a level between 1.120 and 1.080;
   (iii) adding yeast or yeast culture to the mixture and stirring the mixture to add oxygen and to release accumulated heat created during primary fermentation;
   (iv) punching down a layer of solid ginseng content that forms on top of the mixture during the primary fermentation and stirring the mixture to impart ingredients and flavor from the solid ginseng to the mixture;
   (v) after primary fermentation until the specific gravity reading reaches 1.020 or less, racking free-run wine off lees of primary fermentation mixture into a sterilized secondary fermentor;
   (vi) pressing said lees to release additional wine which is combined with the free-run wine and anaerobically fermenting the wine in the secondary fermentor;
   (vii) racking the wine at a specific gravity reading of about 0.998 to about 0.995 after the anaerobic fermentation into a sterilized container, and further anaerobically fermenting the wine; and
   (viii) racking the wine again into a sterilized container to produce ginseng wine.

17. The process according to claim 16, wherein the alcohol content is 17%.

* * * * *